United States Patent
Ozaki et al.

(10) Patent No.: US 8,435,393 B2
(45) Date of Patent: *May 7, 2013

(54) INSTRUMENT AND SYSTEM FOR PHARMACOLOGIC MEASUREMENT AND WELL VESSEL USED THEREIN

(75) Inventors: Nobuhiko Ozaki, Osaka (JP); Hiroaki Oka, Osaka (JP)

(73) Assignee: Panasonic Corporation, Osaka (JP)

( * ) Notice: Subject to any disclaimer, the term of this patent is extended or adjusted under 35 U.S.C. 154(b) by 659 days.

This patent is subject to a terminal disclaimer.

(21) Appl. No.: 12/692,104

(22) Filed: Jan. 22, 2010

(65) Prior Publication Data

US 2010/0133122 A1    Jun. 3, 2010

Related U.S. Application Data

(63) Continuation of application No. 11/213,961, filed on Aug. 30, 2005, now Pat. No. 7,678,249, which is a continuation of application No. PCT/JP2004/008685, filed on Jun. 15, 2004.

(30) Foreign Application Priority Data

Jun. 27, 2003  (JP) ................................. 2003-184161

(51) Int. Cl.
G01N 33/487 (2006.01)
(52) U.S. Cl.
USPC ....... 204/403.01; 204/406; 205/775; 205/792
(58) Field of Classification Search ............. 204/403.01, 204/406; 205/775, 792.5
See application file for complete search history.

(56) References Cited

U.S. PATENT DOCUMENTS 5,187,069 A    2/1993  Shore et al.
5,563,067 A    10/1996  Sugihara et al.
(Continued)

FOREIGN PATENT DOCUMENTS

EP    0 823 483    2/1998
JP    6-78889    3/1994
(Continued)

OTHER PUBLICATIONS

M. Krause et al., "*Extended Gate Electrode Arrays for Extracellular Signal Recordings*", Sensors and Actuators B 70 (2000) pp. 101-107.

*Primary Examiner* — Keith Hendricks
*Assistant Examiner* — Bach Dinh
(74) *Attorney, Agent, or Firm* — Wenderoth, Lind & Ponack, L.L.P.

(57) ABSTRACT

An instrument is provided for pharmacologic measurement capable of detecting a very small and short time change in electric signal caused by a pharmacologic action of a biologic specimen with quickness and a high sensitivity by steeply decreasing an external disturbance component mixed into the system while dropping/exchange of medicinal solutions is conducted in a batch mode. The pharmacologic measurement instrument detects a change in electric signal caused by a pharmacologic action or electrophysiologic action of a biologic specimen, and includes an electrically conductive box having an opening section at the top surface thereof and a well vessel disposed in the opening section thereof, wherein the well vessel includes a base having recesses in which the biologic specimens are put; measurement electrodes formed on the bottom surfaces of the respective recesses; and reference electrodes electrically insulated from the respective measurement electrodes, and the reference electrodes together with the electrically conductive box electrostatically shields the well vessel.

21 Claims, 13 Drawing Sheets

U.S. PATENT DOCUMENTS

| | | |
|---|---|---|
| 5,810,725 A | 9/1998 | Sugihara et al. |
| 5,910,878 A | 6/1999 | Mello et al. |
| 6,151,519 A | 11/2000 | Sugihara et al. |
| 6,682,649 B1 | 1/2004 | Hansen et al. |
| 6,730,199 B1 * | 5/2004 | Hanni et al. ............. 204/403.02 |
| 6,984,297 B2 * | 1/2006 | Nisch et al. ............. 204/403.01 |
| 2002/0063067 A1 | 5/2002 | Bech et al. |
| 2003/0022387 A1 | 1/2003 | Oka et al. |
| 2003/0113833 A1 | 6/2003 | Oka et al. |
| 2004/0106139 A1 | 6/2004 | Oka et al. |

FOREIGN PATENT DOCUMENTS

| | | |
|---|---|---|
| JP | 6-296595 | 10/1994 |
| JP | 9-289886 | 11/1997 |
| JP | 2949845 | 7/1999 |
| WO | 97/27318 | 7/1997 |
| WO | 99/34202 | 7/1999 |
| WO | 02/29402 | 4/2002 |
| WO | 02/055653 | 7/2002 |

* cited by examiner

INSTRUMENT AND SYSTEM FOR PHARMACOLOGIC MEASUREMENT AND WELL VESSEL USED THEREIN This application is a Continuation of U.S. application Ser. No. 11/213,961, filed Aug. 30, 2005 now U.S. Pat. No. 7,678,249, which is a continuation of International Application No. PCT/JP2004/008685, filed Jun. 15, 2004.

BACKGROUND OF THE INVENTION

1. Field of the Invention

This invention relates to an instrument and system for pharmacologic measurement measuring a change in electric signal caused by a pharmacologic action or an electrophysiologic action of a biologic specimen, and a well vessel used therein.

2. Description of the Related Art

Conventionally, there has been known a technique for measuring the electrophysiologic action of a cell. Such a technique is used in, for example, screening medicines with the electrophysiologic action of the cell as an index. The electrophysiologic action of a cell mainly refers to an activity of an ion channel. In a cell, ion concentrations inside and outside the cell membrane change in company with a change in ionic permeability corresponding to the activity of an ion channel. Therefore, the measurement of a change in potential at a cell membrane enables measurements of activity of an ion channel (an electric action of a cell) such as the time required for gating of an ion channel, the timing thereof and the number of times of gating of the ion channel.

As a method for measuring a change in potential at a cell membrane, a method has been known in which an electrode for measuring an extracellular potential made of glass or an electrode made of a metal (such as platinum) is installed in the vicinity of a cell using a micromanipulator or the like to thereby measure the change. As another method, there has been a method in which a similar electrode is stuck into a cell to thereby measure a change in intracellular potential.

According to the above methods, an activity of an ion channel of a cell can be measured quantitatively and minutely. Skill in the technique is required in preparation or operation of an electrode and much time is required in measurement of one specimen, which makes the methods not suitable for high speed screening covering a great amount of compounds of medicine candidates. In addition, it is easy to damage a cell with these methods.

A quantitative measurement on an ion channel conducted in an electrode sticking method is not necessarily required in application of a high speed medicine screening, especially in first screening (selection of first candidates) and in the application, a qualitative detection of closing/opening of an ion channel satisfies requirement and quickness and convenience are given a more serious consideration; therefore, it is thought that an extracellular potential recording method using a flat plate electrode is suitable for such an application (JP No. 2949845, U.S. Pat. Nos. 5,810,725, 5,563,067, JP A No. 9-526737 and U.S. Pat. No. 5,187,069).

An extracellular potential recording method using a flat plate electrode is based on a principle that by placing a flat plate electrode on a biologic specimen in a solution having a composition close to an intravital salt concentration to measure a change in potential at an electrode, an ionic flow passing through an ion channel can be measured. That is, the method uses a phenomenon that an electrophysiologic action of a cell causes a change in potential at the electrode installed in the vicinity of the cell.

Because this extracellular potential recording method only involves placing a cell on a flat plate electrode without sticking an electrode into a cell, an electrophysiologic action of a cell can be measured conveniently and quickly. Since a semiconductor processing technique can be applied in preparation of a flat electrode, a great number of microelectrodes can be formed on a base substrate. Hence, the method is suitable for a high speed screening in various kinds of medicines.

A change in electric signal caused by an electrophysiologic action of a cell is, however, very weak and becomes weaker since such a change in signal is detected through a solution in an extracellular potential recording method using a flat plate electrode. Therefore, in order to ensure a high precision measurement, a necessity arises for detection of a change in electric signal caused by an electrophysiologic action of a cell with good sensitivity.

In order to detect a microsignal with a good S/N ratio, it is required that, generally, a measurement section should be electrostatically shielded so that an external disturbance noise is mixed into a measurement system (M. Krause, S. Ingebrandt, D. Richter et al., Extended gate electrode arrays for extracellular signal recordings, Sensor and Actuators B 70 (2000) pp. 101 to 107). In order to use the method in application to a high speed screening in medicines, all of a measurement section cannot be electrostatically shielded. High speed screening in various kinds of medicines requires exchange of plural kinds of medicinal solutions in a short time with a simple construction. Hence, construction of a sensor base substrate and an apparatus is more complex in mechanisms each injecting/discharging a solution are individually provided to respective solution holding sections and at the same time transferring of the solutions to be controlled. Exchange of medicinal solutions is realized in a following way. XY moving type solution injecting/discharging devices in a row are driven above the solution holding sections so as to add or suck the solutions each having a prescribed unit volume to or from the solution holding sections from above in a batch mode. In the batch mode solution adding/sucking method, however, a necessity arises for forming an opening section through which injection to a solution surface is conducted, which negates electrostatic shielding of the measuring section. As a result, an external disturbance accompanying dropping of a solution is generated at a value as large as not to be neglected relative to a microelectric signal. An external disturbance generated in company with exchange of solutions continues for a long time even after dropping of a solution is over. Hence, a problem arises that it is impossible to measure a response of an ion channel caused by a reaction on a small scale with a medicine and a response of gating of ion channel in rapid inactivation in which the ion channel is activated within a short time from exchange of medicines and thereafter, inactivated.

SUMMARY OF THE INVENTION

The invention has been made in order to solve the above problem and it is an object of the invention to provide an instrument and system for pharmacologic measurement capable of detecting a very small and short time change in electric signal caused by a pharmacologic action of a biologic specimen quickly and with high sensitivity by a method of steeply decreasing an external disturbance component mixed into dropping/exchange of medicinal solutions in a batch mode and to provide a well vessel used therein.

The inventors have conducted studies and have found that a cause of generating an external disturbance described above is an electric bias in a solution generated instantly when an ionic measurement solution is injected into a well vessel to thereby produce a current. The electric bias is very small, but not negligible in the measurement. Also, the external disturbance can be suppressed by electrostatically shielding a well vessel.

A pharmacologic measurement instrument concerning the invention, which has been made based on this finding, is a pharmacologic measurement instrument for detecting an electric signal caused by a phamacologic action or electrophysiologic action of a biologic specimen, which comprises an electrically conductive box having an opening section; and
 a well vessel disposed in the opening section,
 wherein the well vessel comprises:
 a base substrate having well recesses in which the biologic specimens are put or placed;
 a measurement electrode formed on each bottom surface or back surface of the respective well recesses; and
 a reference electrode electrically insulated from the respective measurement electrodes, and positioned for electrostatically shields the well vessel together with the electrically conductive box.

Herein, the term "electrically shielding" means to suppress generation of an external disturbance and it has been found that "electrically shielding" can be realized by broadening the reference electrode as largely as to enable an electromagnetic wave to be shielded or by shunting a great quantity of current by connecting the reference electrodes to the electrically conductive box.

Therefore, a preferable pharmacologic measurement instrument according to the present invention is characterized in that the reference electrodes are electrically connected to the electrically conductive box. By electrically connecting the reference electrodes to the electrically conductive box in such away, a current generated when an ionic solution is injected into the shield opening section from a solution reservoir installed outside the shield or discharged through the shield opening section is caused to flow to the electrically conductive box, thereby enabling an external disturbance component to be steeply decreased.

Another preferable pharmacologic measurement instrument according to the present invention is characterized in that the reference electrodes are formed so as to cover the top part of the well vessel except for the well recesses. By forming such a broad reference electrode, the reference electrode can function as part of a shield. With a large area of the reference electrode immersed in a measurement solution, a current generated when a measurement solution is injected can be instantly shunted not to generate an external disturbance. In addition, no generation of an external disturbance enables a high speed screening in a batch mode to be realized.

By adopting a construction in which the generation of an external disturbance is suppressed, a phamacologic measurement instrument according to the present invention has a construction in which plural injection/discharge devices, each capable of injecting and discharging a solution containing a biologic specimen into a corresponding recess are arranged and the injection/discharge devices, are slidable, thereby enabling injection into the well recesses to be realized. With such a construction, a measurement solution can be injected into the plural recesses in a short time.

In order to measure a microcurrent, it is preferable to install a signal amplifier; however, the signal amplification section is also affected by an external electromagnetic wave in the course of measurement. Therefore, the signal amplification section is also electrostatically shielded. A pharmacological measurement instrument according to the present invention includes first signal amplification sections electrically connected to the respective measurement electrodes, the first signal amplification sections being arranged in the electrically conductive box. Since the first signal amplification sections are electrostatically shielded by the reference electrodes and the electrically conductive box, the signal amplification sections are not necessary to be installed separately from the instrument, thereby enabling the instrument to be simplified in construction.

It is preferable in the present invention to form an insulating section between each of the measurement electrodes and the corresponding reference electrode and the insulating sections have no toxicity to an organism. This is because no adverse influence is exerted to a biologic cell to be measured.

In the present invention, a construction may also be adopted in which each of the well recesses has an inversely tapered sidewall increasing a diameter thereof upwardly, each of the reference electrodes is formed at the corresponding recess sidewall and a corresponding insulating section is formed between the corresponding measurement electrode and the corresponding reference electrode by removing a part of the corresponding reference electrode in the vicinity of the corresponding inversely tapered sidewall and adjacent to the corresponding measurement electrode located at the bottom surface of the corresponding well recess. With such a construction adopted, an insulating property between the reference electrode and measurement electrode can be increased without providing a spacer or the like.

It is preferable to provide at least one through hole in the bottom surface of each of the recesses on the base substrate and to form the corresponding measurement electrode at a position where a biologic specimen fixed in the corresponding through hole and the corresponding measurement electrode are connected to each other. With such a structure adopted, the biologic specimen can be held so as to be in close contact with the measurement electrode, which improve a measurement sensitivity, and which makes it possible to conduct stable measurement. In addition, it is preferable to provide suction means guiding the biologic specimen into the corresponding through hole in the base substrate.

In the invention, a solution accommodated in a well recess can also be exchanged for another solution.

In a pharmacologic measurement instrument according to the present invention, each of the well vessels is mountable or demountable through the opening section of the electrically conductive box and is disposable. In a case where the well vessel is mountable or demountable and disposable, a great quantity of specimens can be measured at a high speed. Besides, it is also hygienic to use such a disposable vessel. Only well vessels can be exchanged, which is lower in cost than in a case where all of pharmacologic measurement instruments is exchanged.

A pharmacologic measurement system utilizing the invention includes: the pharmacologic measurement instrument and a calculation section data-processing a signal amplified in each of first signal amplification sections.

Furthermore, the pharmacologic measurement system preferably includes a second signal amplification section further amplifying an output signal from each of the measurement electrodes having been amplified in the corresponding first amplification section while causing band limitation thereto.

Furthermore, it is preferable that the pharmacologic measurement system includes an electric stimulus generator applying a desired current at a desired timing to each of the measurement electrodes and further includes a measurement environment adjustment apparatus adjusting a temperature, a humidity and a gas concentration of the pharmacologic measurement instrument to respective desired values.

The invention is directed to a well vessel used in a pharmacologic measurement instrument for detecting an electric signal caused by a pharmacologic action or an electrophysiologic action of a biologic specimen, wherein the well vessel includes:

a base substrate having a number of well recesses into which the biologic specimens are put;

a measurement electrodes formed on each of the bottom surfaces or the back surfaces of the respective well recesses; and a reference electrodes electrically insulated from the respective measurement electrodes, the reference electrode being electrically connected to the electrically conductive box in a mountable/demountable manner. By enabling the well vessel to be demountable from the electrically conductive box, exchange of measurement solutions and cleaning of the well vessel can be realized with ease. Since the well vessel is fabricated so that when the well vessel is mounted to the electrically conductive box, the reference electrodes of the well vessel and the electrically conductive box establish electrical conduction therebetween, the well vessel can be electrostatically shielded in a case where the well vessel is electrically connected to the electrically conductive box, thereby enabling an external disturbance occurring when a solution is injected or discharged to be steeply decreased.

As described above, according to a pharmacologic measurement instrument of the invention, an external disturbance exerts no influence on a sensor in company with dropping/exchange of medicines from above; therefore, many kinds of pharmacologic determination can be done in a short time. Moreover, gating of an ion channel in company with a steep inactivation can be measured, thereby enabling a determination test covering a wide range to be implemented.

DESCRIPTION OF THE INVENTION

Detailed description will be given of the present invention below using the accompanying drawings.

Embodiment 1

(Construction of Pharmacologic Measurement Instrument of Embodiment 1)

Figure 1:
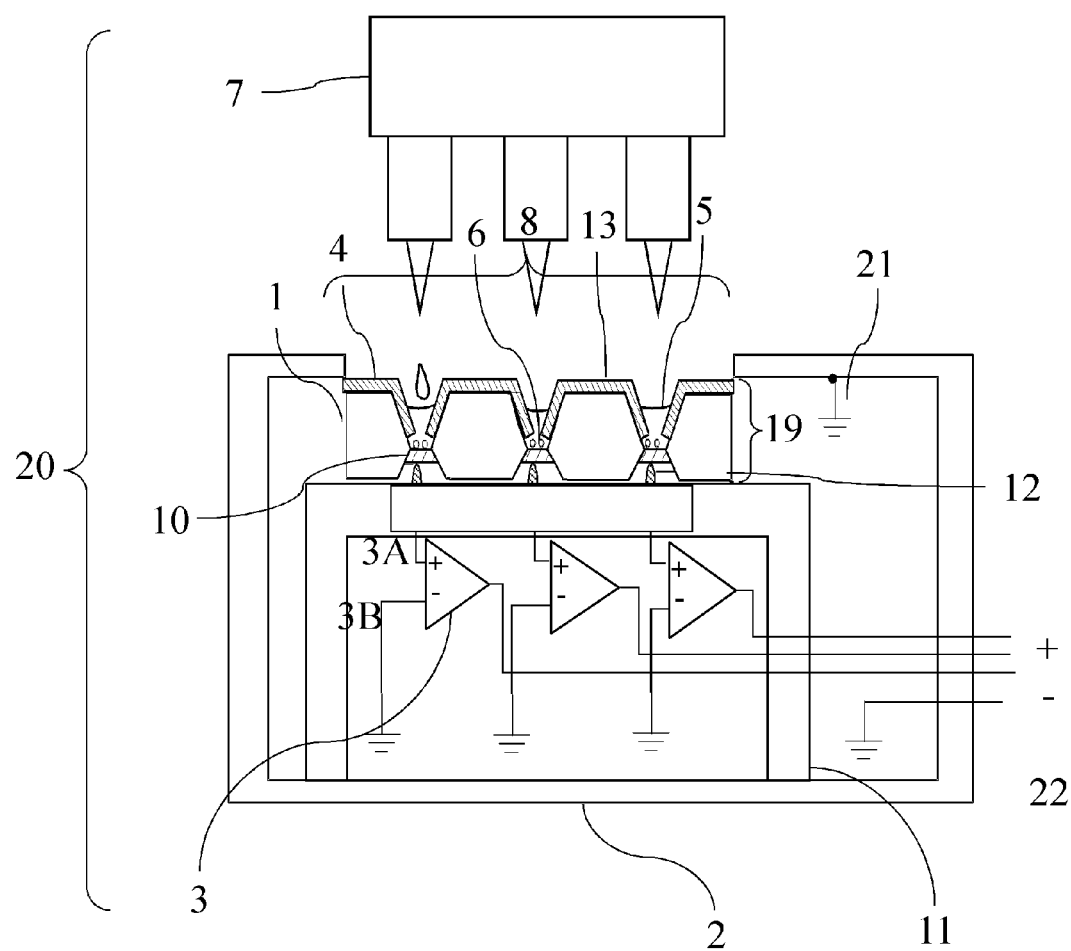
FIG. 1 is a conceptual view, as a mode, showing a construction of a pharmacologic measurement instrument of a first embodiment.

FIG. 1 is a conceptual view, as a mode, showing a construction of a pharmacologic measurement instrument 20 of a first embodiment. The pharmacologic measurement apparatus of the first embodiment has an electrical conductive box 2 having an opening section 8 at the top surface and a well vessel 19 provided in the opening section 8. The well vessel 19 may be either fixable at the opening section 8 of the electrically conductive box 2 or demountable from the opening section 8. The pharmacologic measuring instrument 20, when required, further includes: a solution injection/discharge device 7; preamplifiers (first signal amplifiers) 3 in an electrical conductive box 2; a base substrate placement table 11 for fixing the well vessel 19; measuring electrodes; and contact points 12 electrically connecting the measurement electrodes 10 to respective the preamplifiers (the first signal amplifiers) 3. The number of discharge sections of the solution injection/discharge device 7 is preferably determined so as to be adapted for the number of recess sections in one row arranged on the base to thereby drop a measurement solution in a sliding way.

The well vessel 19 of the first embodiment has: a base 1 on which recesses 4 into which a measurement solution 5 containing a biologic specimen 6 is injected; the measurement electrodes 10 formed on the bottom surfaces of the respective recesses 4; and reference electrodes 13 electrically insulated from the measurement electrodes 10. In measurement, the recesses 4 are filled with the measurement solution 5 and the biologic specimens 6 (hereinafter also referred to as cells 6 as a concrete example) are disposed in the vicinities of the respective measurement electrodes 10.

The reference electrodes 13 are, as shown in FIG. 1, formed all over the top surface of the well vessel 19 except for the bottom surface of the recesses 4 and areas in the vicinities thereof. The reference electrodes 13 are arranged without establishing direct conduction to the measurement electrodes 10 and areas of the reference electrodes 13 are necessary to be sufficiently larger than those of the measurement electrodes in order to decrease noise. This is because with a larger area of a reference electrode, impedance is low and a factor for a change in signal caused by an external disturbance is smaller. A total of areas of the reference electrodes 13 is, to be concrete, desired to be available so as to be of a construction in which the total of areas of the reference electrodes 13 is 5 or more times as large as the total of areas of all the measurement electrodes. The outermost surfaces of the reference electrodes 13 are constituted of a material such as gold, platinum or silver-silver chloride and each thereof can adopt in any shape. The reference electrodes 13 is required to be partly immersed in a culture fluid 5.

An electric signal from a measurement electrode 10 is measured with a potential at a reference potential 13 as a reference. That is, each of the measurement electrodes 10 is connected to one 3A of input terminals of a corresponding preamplifier (a first signal amplifier) 3. The other 3B of the input terminals of the preamplifier 3 is connected so as to be equal to the potential at the reference voltage 13. The input terminal 3B and the reference electrode 13 can also be, as shown in FIG. 1, of a construction in which the electrically conductive box 2 serves as a ground point and the input terminal 3B and the reference electrode 13 are thereby equal in potential to each other. The preamplifier 3 is placed in the electrically conductive box 2 to thereby enable a potential at the measurement electrode 10 at a position very close thereto to be measured. With such a construction adopted, a microsignal measured at the measurement electrode 10 can be obtained at a good S/N ratio in a low noise environment.

The well vessel 19 is disposed in the opening section 8 of the electrically conductive box 2 and the reference electrodes 13 are electrically connected to the electrically conductive box 2. With such a construction adopted, an opening area not electrostatically shielded through which a solution is dropped in a batch mode can be reduced to only part of the recesses 4, thereby enabling a change caused by an external disturbance accompanying an exchange of solutions to be reduced.

Figure 2:
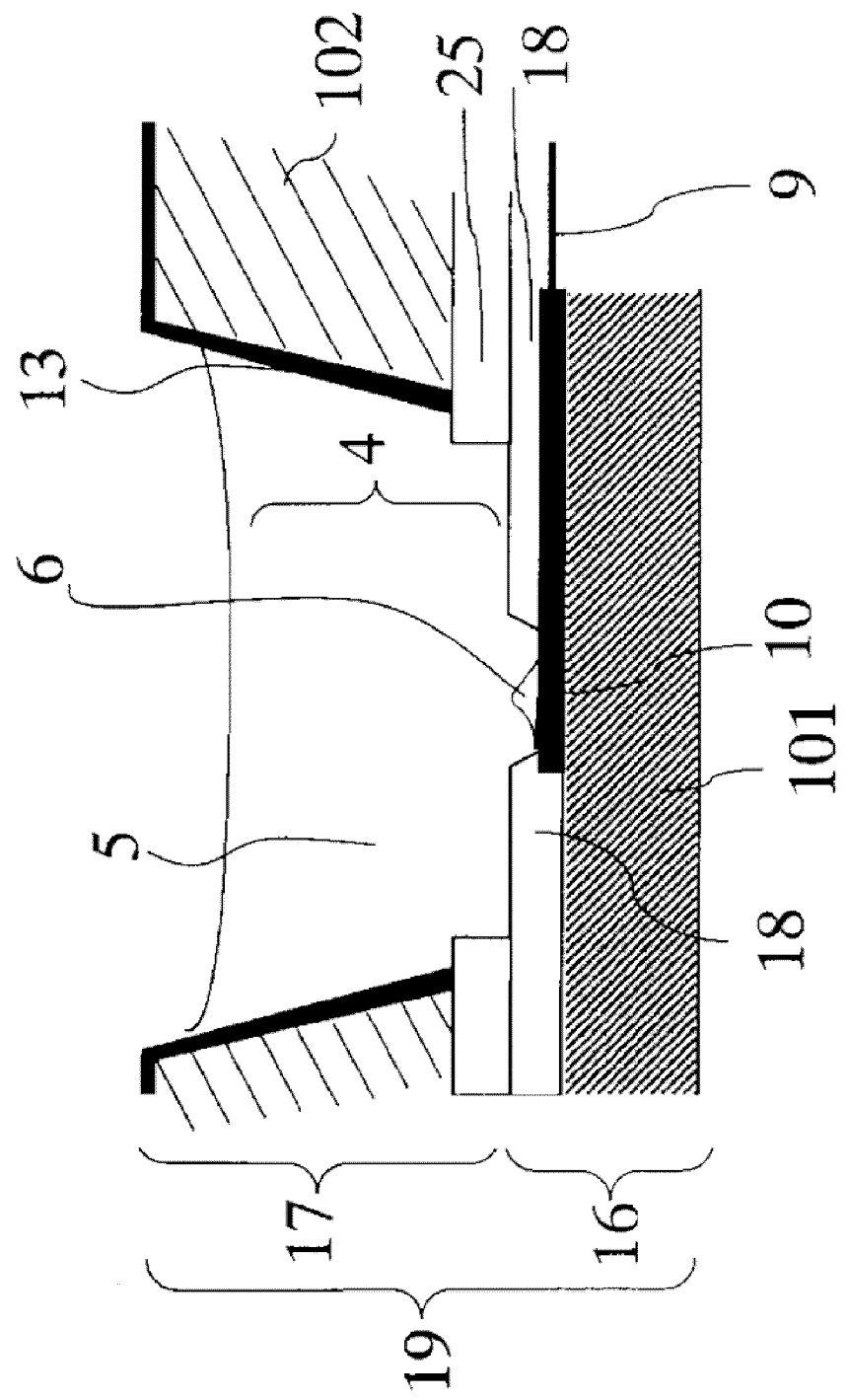
FIG. 2 is a partially sectional view showing an example of a well vessel of the first embodiment.
Figure 3:
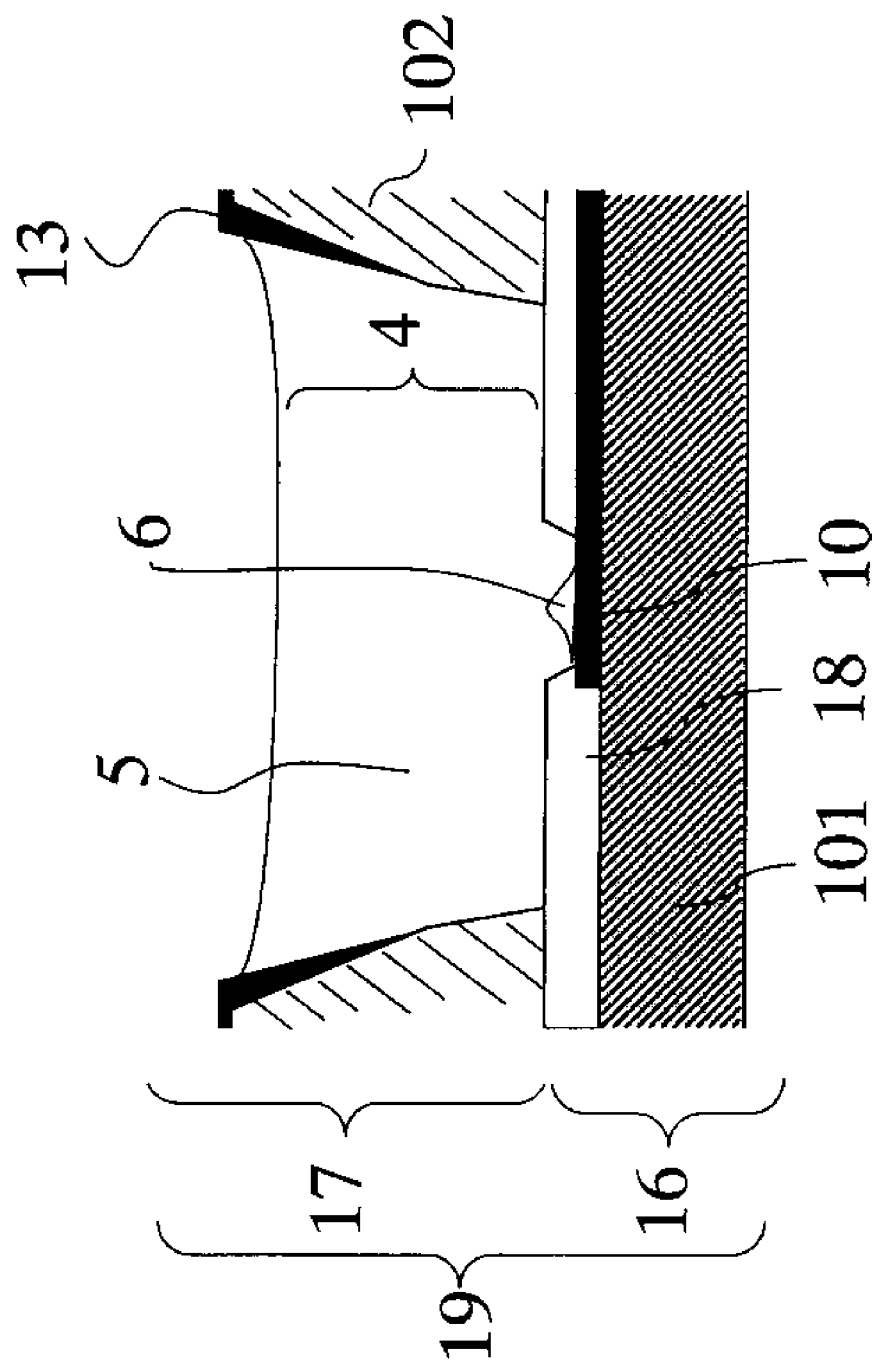
FIG. 3 is a partially sectional view showing an example of a well vessel of the first embodiment.

Then, in FIGS. 2 and 3, one example of a detailed construction of a part containing one measurement electrode of the well vessel 19 is shown. From the viewpoint of a fabrication process, the well vessel 19 is constructed of a sensor base substrate 16 prepared by forming the measurement electrode 10 on a base substrate 101 and a solution holding section 17 capable of holding a measurement solution 5 with a recess 4 (hereinafter referred to a frame or a hole according to a situation) provided on the upper base 102. That is, the base 1 of FIG. 1 is formed with the base substrate 101 and the upper base 102 and the inside of the recess 4 serves as a cell culture region. The recess 4 is desirably in the shape of an inverse truncated cone. With such a construction adopted, cells incubated in integrated microregions can be optically observed using a reflecting light from above.

A material of the base substrate 101 is desirably of a high electric resistance and insulating. The base substrate 1 can be preferably formed with a material that can easily be fine patterned. Examples thereof, to be concrete, include: semiconductor materials represented by single crystal silicon, amorphous silicon, silicon carbide, silicon oxide, silicon nitride and others; composite materials of the semiconductors represented by a silicon-on-insulator (SOI); and inorganic insulating materials selected from the group consisting of glass, quartz glass, alumina, sapphire, forsterite, silicon carbide, silicon oxide and silicon nitride; organic materials selected from the group consisting of a polyethylene, ethylene, polypropylene, polyisobutylene, polyethylene terephthalate (PET), unsaturated polyester, fluororesin, polyvinyl chloride, polyvinylidene chloride, polyvinyl acetate, polyvinyl alcohol, polyvinyl acetal, acrylic resin, polyacrylonitrile, polystyrene, acetal resin, polycarbonate (PC), polyamide, phenol resin, urea resin, epoxy resin, melamine resin, styrene-acrylonitrile copolymer, acrylonitrile-butadiene styrene copolymer, silicon resin, polyphenylene oxide, polysulfone and the like. Preferable are single crystal silicon, SOI, PET, and PC.

A measurement electrode 10 is made of an electrically conductive material such as a metal material, a metal oxide material or an electrically conductive high polymer capable of being laminated in layers on the base substrate 1. Examples of metal materials include: metal materials selected from the group consisting of platinum, platinum black, gold, palladium, rhodium, silver and tungsten. Examples of metal oxides include: materials selected from the group consisting of titanium oxide, tin oxide, manganese oxide, lead oxide and ITO (indium tin oxide). A layer made of a different metal can be deposited between the first layer and the base substrate in order to deposit a material mentioned above on the outermost surface thereof. Examples of materials preferably used for the purpose are selected from the group consisting of nickel, chromium, ITO, tungsten, titanium, tin, manganese, lead and alloys thereof. The measurement electrode 10 may be covered by either an electrically conductive high polymer or a monomolecular film. Electrode materials similar to those described above can be applied to a lead line 9 connected to the measurement electrode 10.

Figure 4:
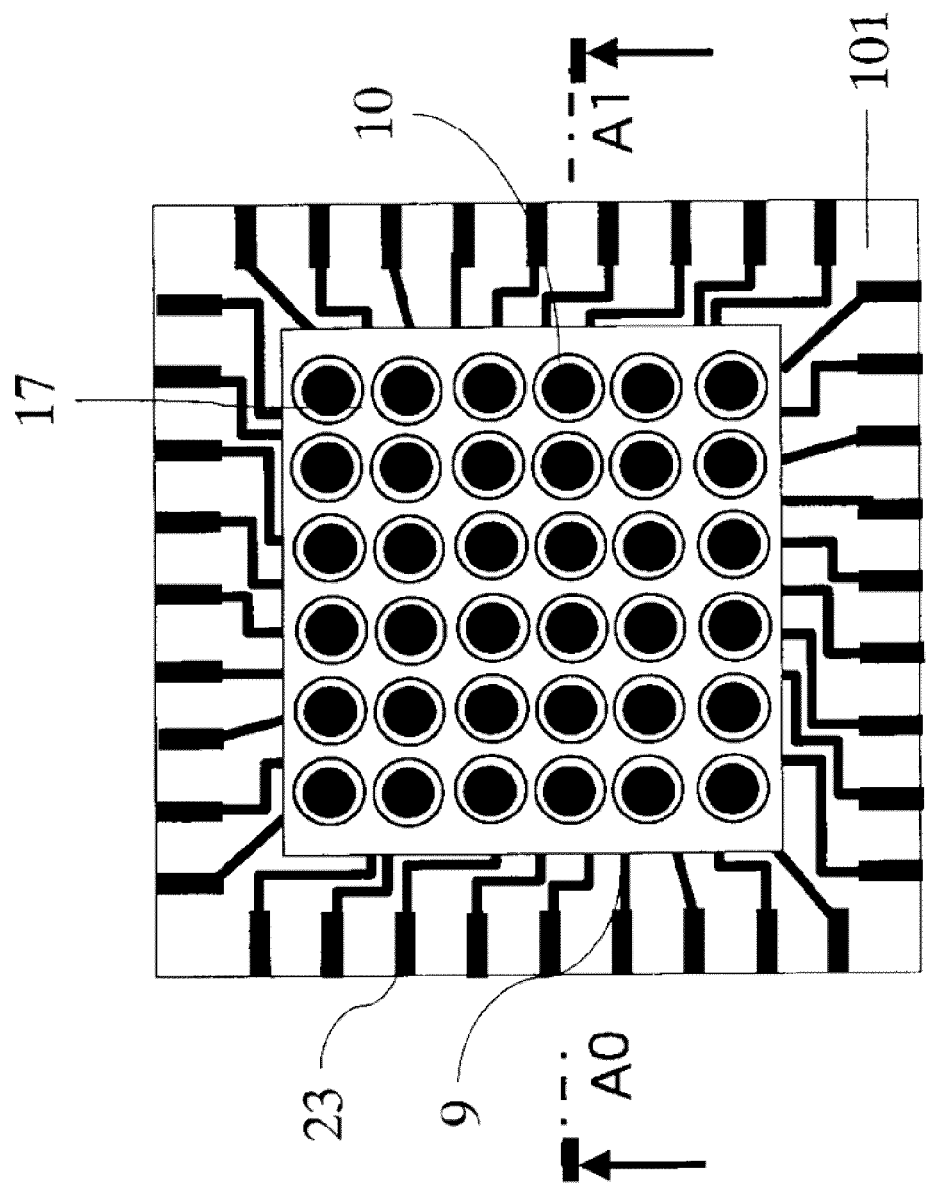
FIG. 4 is a top plan view of the well vessel of the first embodiment (a reference electrode 13 is omitted).
Figure 5:
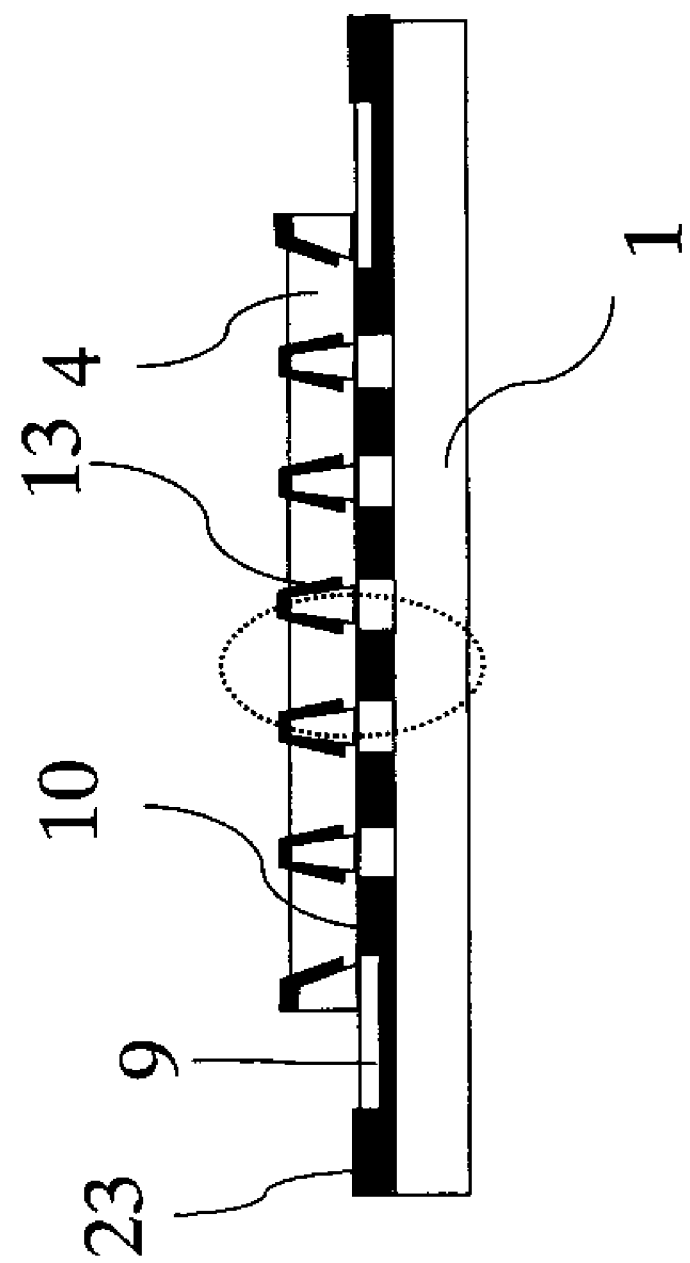
FIG. 5 is a view taken on line A0-A1 of a well vessel of FIG. 4.

Then, in FIGS. 4 and 5, there is shown an example construction of a well vessel 19 having plural measuring electrodes. FIG. 4 is a top plan view and FIG. 5 is a section taken on line A0-A1 of a well vessel of FIG. 4. A part encircled by a dotted line in FIG. 5 corresponds to a well vessel containing one measurement electrode. A way of arrangement of plural well vessels may be of either a construction in which one measurement electrode 10 is installed in one recess (frame) or a construction in which plural electrodes 10 are installed in one recess 4. The construction in which one measurement electrode 10 is installed in one recess 4 is useful, for example, for a case where a medicinal responsibility of a cell fixed on each electrode 10 is measured, while the construction in which plural measurement electrodes 10 are installed in one recess 4 enables, for example, a network to be formed among neurons fixed on the respective electrodes 10, which is useful for an analysis of the network.

(Fabrication Method for a Well Vessel of the Pharmacologic Measurement Instrument of Embodiment 1)

Description will be given of a fabrication method for the well vessel 19 of the pharmacologic measurement instrument 20 of the first embodiment. The well vessel 19 of FIGS. 2 and 3 is formed in a process including a step of preparing a sensor base 16, a step of preparing a solution holding section 17 and a step of adhering the sensor base substrate 16 and the solution holding section 17.

Description will be given of a fabrication method for the sensor base substrate 16 of the well vessel 19. An electrode material described above is vapor deposited on the base substrate 1 and thereafter, the base substrate 1 is etched with a photoresist thereon to thereby form a desired pattern having plural pairs each of which is constituted of an electrode 10 and a corresponding lead line 9. Note that formation of a pattern of the electrodes 10 can be implemented with a mask method in which the electrodes 10 are vapor deposited through a stensil mask on which an electrode pattern is formed in advance and a lift-off method. Thereafter, the lead line 9 except for an external connection section is covered with an insulating film 18 and thereafter, the base substrate is diced into small square pieces each having a side of a prescribed length and one small pieces is used as the sensor base substrate 16. One pair of an electrode 10 and a lead line 9 are formed on the one small pieces.

The desired pattern includes one electrode 10 formed almost at the center of each small piece and a shape of an electrode 10 is typically square or circular and a length of one side or a diameter can be in the range from about 1 to about 2000 μm. In a case where a size of an electrode 10 is larger than the biologic specimen 6, measurement of plural biologic specimens 6 can be done with one electrode.

In the well vessel 19 for measuring an electrophysiologic action of one cell, it is preferable to use an electrode 10 in the shape of a circle having a diameter of about 5 μm, for example, in a case where an object to be measured is a cell having a major axis of 15 μm, which is determined according to a size of a cell as the object to be measured. This is because, in this case, it is easy to fix only one cell on the electrode 10, thereby enabling an electric signal caused by an electrophysiologic change of one cell to be measured with ease.

As examples of materials of the insulating film 18 for covering and insulating the lead line 9, there can be named polyimide (PI) resin, acrylic resin, epoxy resin and the like. Preferable is a photosensitive resin such as a negative photosensitive polyimide (NPI). The use of a material of a photosensitive resin enables a pattern formation with photoetching to form a hole in the insulating film 18 on the electrode 10 and to expose only the electrode 10. In such a way, the insulating film 18 is preferably provided so as to cover almost all the surface of the base substrate 101 except for the upper surfaces of the electrodes 10 and an external connection section of the lead line 9 from the standpoint of productivity and the like.

Further, below is a description of a fabrication method for the solution holding section 17 of the well vessel 19. The fabrication method for the solution holding section 17 may be either cut using a technique known to a person skilled in the art or fabricated with a photolithographic method. Especially shown is one of example fabrication of the reference electrode 13. The fabrication process of the reference electrode 13 with such a construction adopts a metal deposition method such as vapor deposition or sputtering, electroplating or electroless plating. In a case where the reference electrode 13 is fabricated using a metal deposition, the solution holding section 17 is mounted on a rotary stage of a deposition apparatus with an inclination relative thereto to thereby enable a target metal to be deposited on the sidewall of the frame 4 with ease. Description will be given of a process for fabricating the reference electrode 13 using a plating method. An insulating material is desirably used as a material of the upper base 102 of the solution holding section 17. Preferably used are, for example, acrylic resin and ABS resin. Masking is applied on the lower surface and side surface of the upper base 102 formed with ABS resin on which chemical plating can be applied with a method known to a person skilled in the art. A rubber masking agent or a masking tape is desirably used from an aspect of workability. Thereafter, the solution holding section 17 is immersed in a plating bath and chemical copper is electroless plated thereon. Gold can be electroplated on the chemical copper. Through the above steps, the reference electrode 13 is fabricated on the top surface of the upper base 102 and the sidewall of the frame 4. The plating method is desirable from the standpoint of productivity since the plating methods enable a collective, mass processing to be realized as compared with a metal deposition method and further an electrode to be uniformly formed regardless of a shape thereof on the sidewall and others of the frame 4.

Then, the solution holding section 17 is adhered to the sensor base substrate 16. In this step, a necessity arises for a construction in which the measurement electrode 10 formed on the base substrate 101 and the reference electrode 13 formed in the solution holding section 17 do not establish conduction therebetween. A spacer 25 made of an insulator may be inserted between the solution holding section 17 and the sensor base substrate 16 as shown in FIG. 2. The spacer 25 with a hole formed at a position corresponding to the hole 4 desirably has a stickiness from an aspect of sealing of the solution (hereinafter the spacer 25 is also referred to as bonding adhesives). Examples of the bonding adhesives 25 used in such an application include: a silicon rubber sheet and, preferably, an adhesive agent having a component without a toxicity to an organism and an adhesive sheet. To be more concrete, the bonding adhesives 25 can be fabricated with a thermomelting sheet NS-1000 (manufactured by NITTO SHINKO Corporation) or a silicon rubber adhesive of One-Component KE42T (manufactured by Shin-Etsu Chemical Co., Ltd.).

In FIG. 3, there is shown an example of another state of joining a solution holding section 17 and the sensor base substrate 16. It is similar to the case of FIG. 2 that in FIG. 3, the solution holding section 17 and the sensor base substrate 16 are adhered to each other with an adhesive (not shown). In FIG. 3, since an adhesive is inserted therebetween, no necessity arises for securing insulation. In FIG. 3, in order to secure insulation between the electrodes 10 and 13, the recess 4 in the upper base 102 is plated with gold prior to joining of the solution holding section 17 to the sensor base substrate 16, thereafter the hole 4 in the shape of an inverse truncated cone is cut only in the vicinity of the bottom surface thereof using a cutting tool having a different taper from that of the hole 4 to thereby remove the reference electrode 13 in the vicinity of the bottom surface.

(Insertion of Specimen and Preparation for Measurement)

Then, description will be given of an example of a step for fixing a cell on the electrode 10. It is preferable to fix a fixing agent (not shown) in a region in the recess 4 of the well vessel 19. The fixing agent is a material to fix a cell with ease and/or to make fixing of the cell firm. Fixing with a fixing agent may also be conducted prior to placement of the recess (frame) 4.

A dielectric is usually employed as a fixing agent to fix the cell 6. A dielectric preferably used is a polymer having a strongly basic functional group or a strongly acidic functional group. Concrete examples thereof that are preferably used include: positively charged polymers such as polyethylene imine (PEI), polyolornithine (PO) and polylysine (P). A positively charged polymer described above has an additional effect attracting a negatively charged cell. Materials each having a cell adhesion capability similar thereto include a high polymer having a biguanid group or a carbamoylguanidide group. To be concrete, examples thereof that preferably used include allyl biguanid-co-ally amine (PAB), allyl-N-carbamoylguanidino-co-allyl amine (PAC). In addition, a matrix material can be used as a material having a cell adhesion capability. Protein having a cell adhesion property is preferably used as a matrix material and examples thereof include colagen, fibronectin, vitronectin, laminin and others.

Coverage on the electrode 10 with a fixing agent can be achieved in a procedure in which the upper part of the electrode 10 is exposed to a fixing solution obtained by dissolving a fixing agent described above at a prescribed concentration, the fixing solution is removed from the surface when a prescribed time elapses after the exposure and the surface is washed with a cleaning solution at least one time, followed by drying. Another method may be applied in which the fixing solution is locally spread only on the top surface of the electrode 10 to thereby cover the electrode 10.

The coverage of the electrode with a fixing agent exerts no influence on a flatness of the surface of the electrode 10 so as to be adapted for a size of a cell. Therefore, the coverage does not work as a hindrance to fixing of a cell.

Then, the recess 4 of the solution holding section 17 is filled with a culture fluid 5. As culture medium 5, preferably used is a physiological saline containing 20 mM to 400 mM of sodium chloride as a main component and a buffer solution prepared by dissolving a culture medium containing various kinds of nutrients, growth factors, antibiotics, a prescribed chemical material, a compound and a medicine thereinto.

Thereafter, a desired cell is seeded in the culture fluid 5. In a case where an adhering cell is fixed by a fixing agent at the same time as progress in incubation of cells, a cell is fixed on the outermost surface of the electrode 10 by the fixing agent.

When a prescribed time elapses after the cell is fixed, pharmacologic determination is conducted using a pharmacologic measurement system described below.

(High Speed Pharmacologic Measurement System)

A pharmacologic measurement system 30 of the invention includes: a pharmacologic measurement instrument 20; a second signal amplification section 26 causing amplification or a band limitation to a preamplifier output 22 of the pharmacologic measurement instrument 20; and a calculation section 28 data-processing a signal amplified in the second signal amplification section 26. The pharmacologic measurement system 30 further includes: an electric stimulus generator 27; an image pick-up device 29 or a measurement environment adjustment apparatus 24, when required. The pharmacologic measurement system is a simple system and provided as a system to process an output signal as a pharmacologic response of a cell fixed on the measurement electrode 10. That is, in the pharmacologic measurement system 30, a potential at cell membrane of a cell or a change in potential at the cell membrane caused by each of various kinds of medicines provided by the solution injection/discharge device 7 can be measured as a change in voltage due to a change in potential outside a cell.

The pharmacologic measurement system 30 is constructed integrally with the calculation section 28 having a proper measurement software in order to process a preamplifier output 22 of the pharmacologic measurement instrument. An output signal from a cell measured and first-stage amplified in the well vessel 19 is supplied through an output terminal 22 and amplified in the second signal amplification section 26 and limited in frequency band and thereafter, inputted into the computer (calculation section) 28 through an A/D converter. The measurement software provides a parameter setting screen image on which conditions for signal processing and measurement and other can be set; a recording screen image on which a change in potential detected from the cell is recorded and displayed in real time; and a data processing screen image on which recorded data can be analyzed on the screen of the computer.

The pharmacologic measurement system 30 may be a system in which the electric stimulus generator 27 for giving a stimulus signal to a desired measurement electrode 10. The applied stimulus signal sets stimulation conditions for the electric stimulus generator 27. Alternatively, the stimulation conditions are set by the calculation section 28 having a proper measurement softwear. A stimulus signal from the computer 28 is preferably outputted through the D/A converter to the electrode 10 and an output signal from a cell may be amplified by the signal amplification device 26. Only a spontaneous potential generated in a cell can be naturally measured by the pharmacologic measurement system 30 without giving an stimulus signal from the electric stimulus generator.

The pharmacologic measurement system 30 may include the image pick-up device 29 picking up or observing the electrode 10 provided in the well vessel 19; the measurement environment adjustment apparatus 24 for keeping the well vessel 19 at a prescribed temperature, a gas concentration and a humidity; and others.

Embodiment 2

Figure 6:
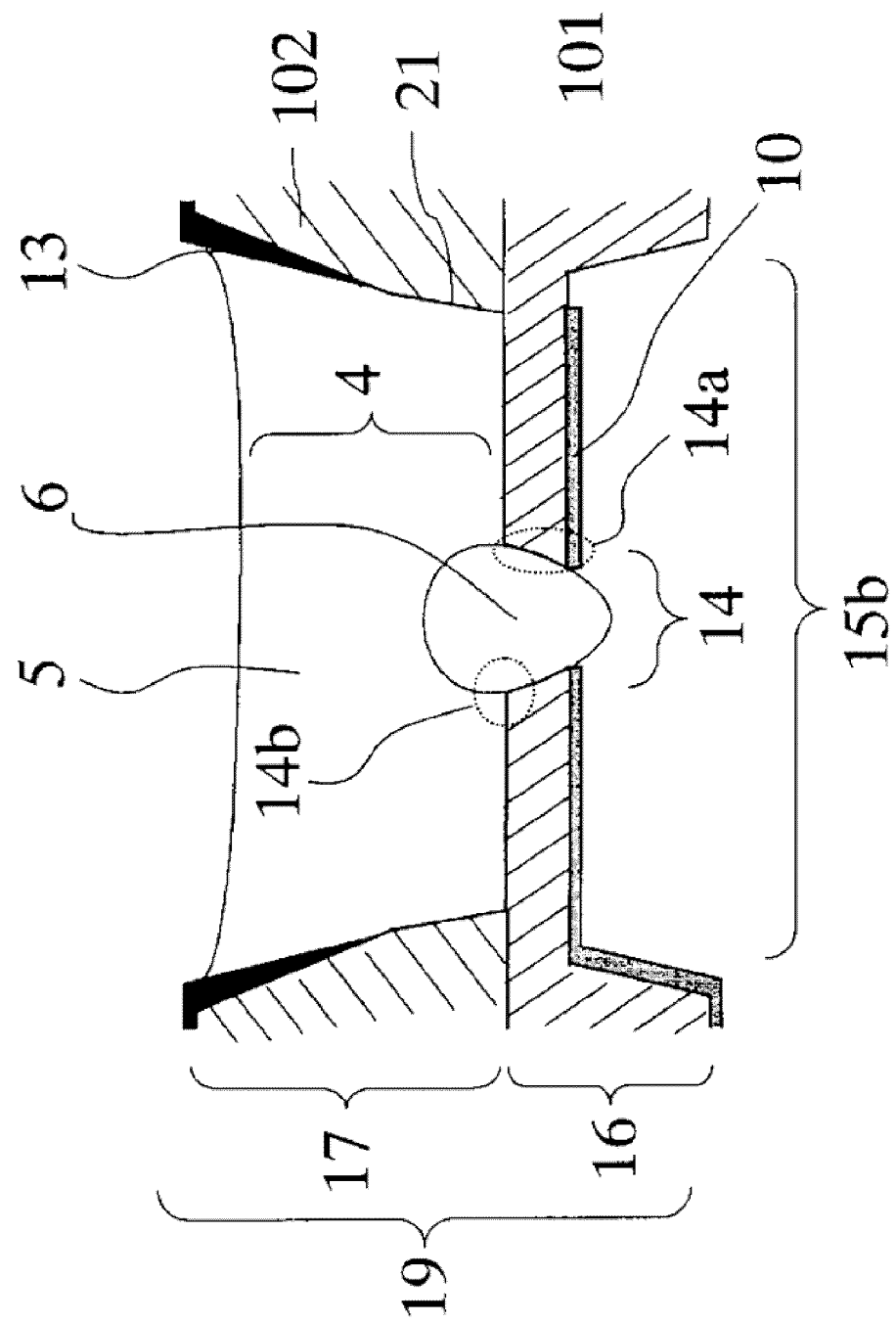
FIG. 6 is a partially sectional view showing an example of a well vessel of a second embodiment.
Figure 7:
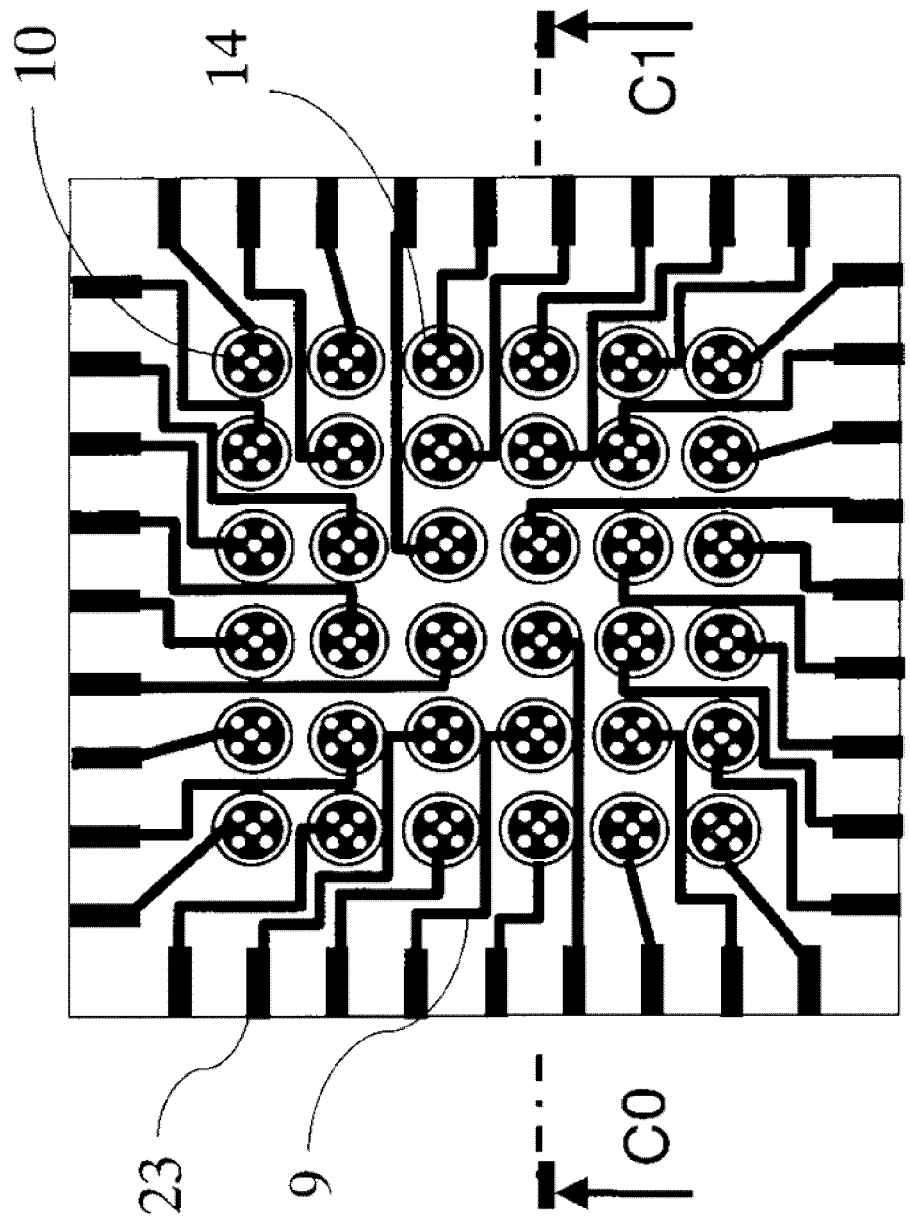
FIG. 7 is a top plan view of the well vessel of the second embodiment.
Figure 8:
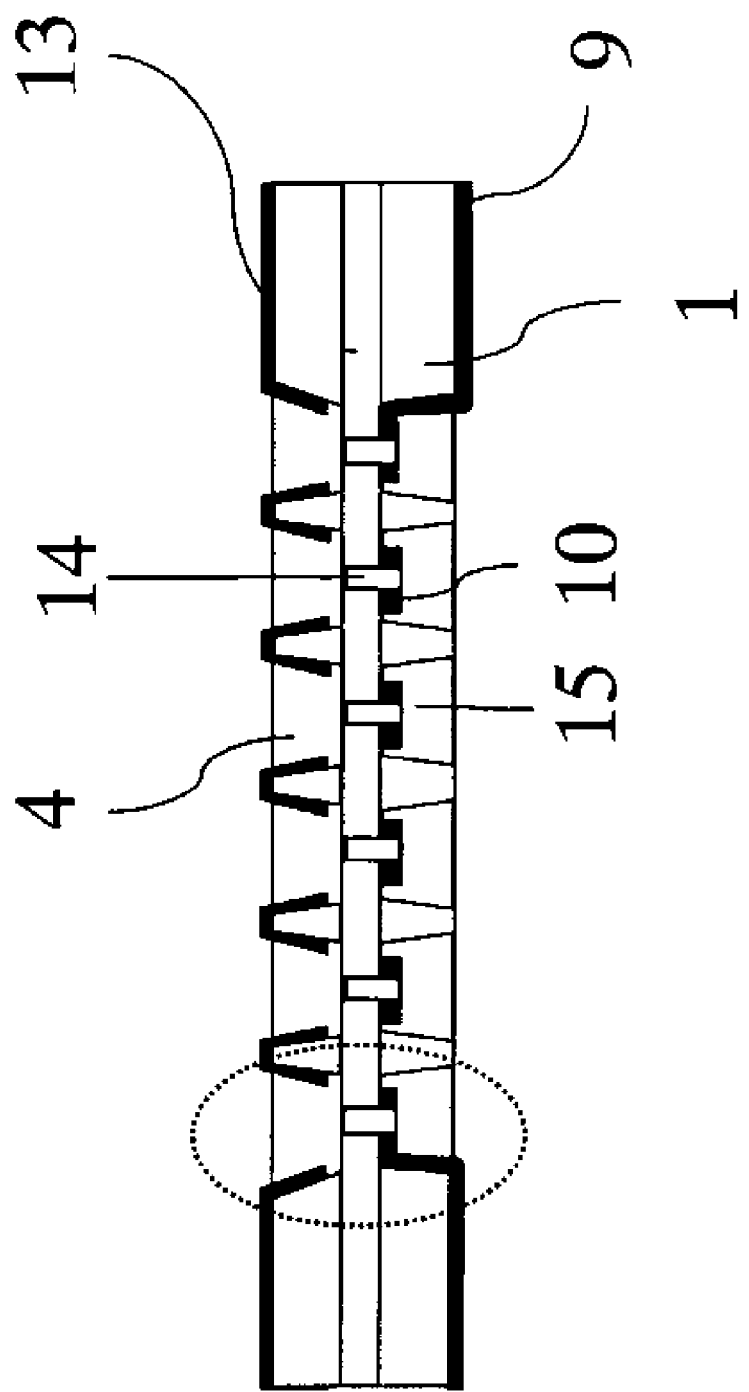
FIG. 8 is a view taken on line C0-C1 of the well vessel of FIG. 7.
Figure 9:
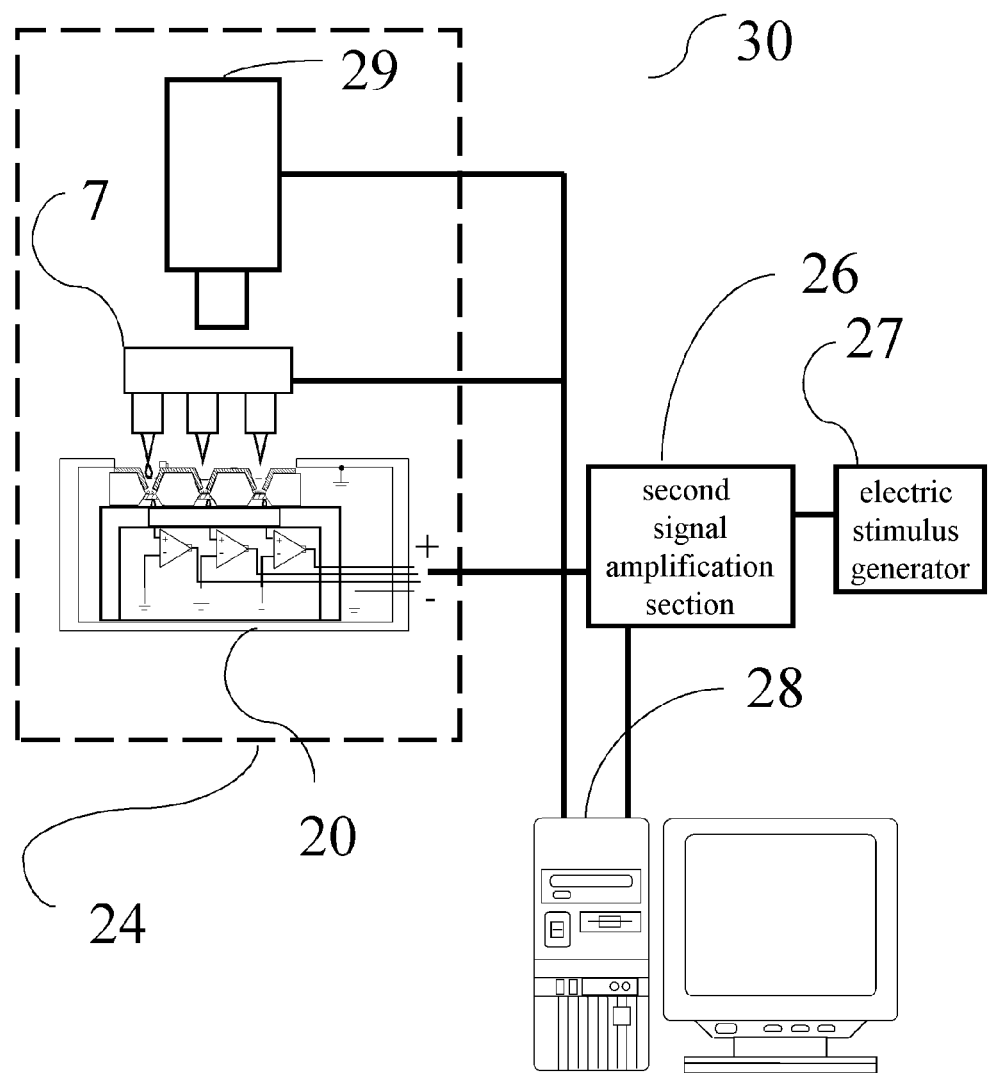
FIG. 9 is a conceptual view, as a mode, showing a construction of a pharmacologic measurement instrument of the invention.

The second embodiment is related to a pharmacologic measurement instrument provided with electrodes each having a construction different from that in the first embodiment. FIG. 6 is a sectional view, as a model, showing a structure of a well vessel 19 of a pharmacologic measurement apparatus of the second embodiment. FIG. 7 is a construction in which the electrodes 10 are disposed at intersections in a square array of 6 rows and 6 columns. FIG. 8 is a sectional view taken on line C0-C1 of the well vessel of FIG. 7. A part of FIG. 8 encircled with a dotted line corresponding to a well vessel including one measurement electrode. While in FIG. 6, there is shown a well vessel 19 in which only one measurement electrode 10 is formed in the recess (frame) 4, a construction may be adopted in which plural electrodes 10 and corresponding lead lines 9 are formed in the frame 4, which is similar to that in the first embodiment. Note that since in the sensor base substrate 16 of the second embodiment, no wiring is formed on the back surface of the sensor base substrate 16, no necessity arises for the sensor base substrate 16 and the solution holding section 17 to be separately formed from each other using the base substrate 101 and the upper base 102 and to be then joined to each other and it is also possible to form recesses 4 and electrodes 10 and 13 on the base substrate 1 in one piece.

The well vessel 19 of the second embodiment is different from that shown in FIG. 1 only with respect to a construction of the sensor base 16, therefore, description of parts except for the sensor base substrate 16 is omitted.

The sensor base substrate 16 has the through hole 14. A biologic specimen is adhered in close contact by the through hole 14. No specific limitation is placed on a shape of the through hole 14 and any shape may be adopted as far as a biologic specimen as an object is held. In FIG. 6, the through hole 14 is shaped so as to be a large cylinder having the upper opening section larger than the lower opening section. A size of the through hole 14 can be determined arbitrarily depending on a biologic specimen as an object and no specific limitation is placed on a size thereof as far as it is a size with which the biologic specimen as an object is held. A concrete size of a through hole 14 is almost 20 µm in a case where a diameter of the opening section above the upper surface of the sensor base substrate 16 is in the range from 10 to 500 µm and desirably in the range from 10 to 100 µm and a major axis of a cell used as a biologic specimen is almost 30 µm as a more preferable example.

The through-holes 14 are of a construction in which plural through holes are formed for one electrode 10, which is shown in FIG. 14. The number of the through holes 14 and positional relations thereof are arbitrary. The positional relations can be, for example, radial as shown in FIG. 7. In the example modification, electrical signals caused by cells 6 held in the plural through hole 14 are detected as one electric signal from the one electrode 10. The example modification is useful for medicine screening detecting responses from the plural cells.

A method for forming a through hole or through holes 14, which is different according to a material of the base substrate 1, is a method using excimer laser, for example, in a case where the base substrate 1 is made from PET. A through hole or through holes can be formed by etching, for example, in a case where the base substrate 1 is made of an Si wafer.

By connecting a through hole 14 to cell suction means from under, holding of a cell in the through hole 14 can be firmer, which increase measurement sensitivity and measurement stability. With this construction adopted, even a floating cell can be held in the through hole 14.

In the sensor base substrate 16, an electrode 10 is formed on a hole wall surface 14a of the through hole 14 or the periphery 14b of the opening section of the hole. The lead line 9 is formed on the back surface of the sensor base substrate 16 so that the lead line 9 is connected to the electrode 10. The lead line 9 connected to the electrode 10 is, in a case, insulation-covered. The electrode 10 is formed by attaching a electrode material to the hole wall surface 14a of the through hole 14 and the periphery 14b of the opening section of the through hole 14 with a vacuum evaporation method or a sputtering method.

A shape of the through hole 14 may be either in the shape of a cylinder as shown in FIG. 8 or as another example, in the shape of an inverse truncated cone. For example, in a case where a through hole 14 in the shape of a cylinder is hard to be formed in a single pass of a cutting tool because of an excessively larger thickness of the base substrate 1, recess holes may be formed from the upper surface and the lower surface and then, the recess holes are caused to pass therethrough to thereby form a perfect through hole 14 as shown in FIG. 6.

EXAMPLES

The invention is exemplified in a more concrete way. It should be understood that the examples are not intended to limit the invention in any way.

Example 1

The pharmacologic measurement instrument of a first embodiment shown in FIG. 1 was fabricated by way of trial as Example 1. The pharmacologic measurement instrument of a conventional construction shown in FIG. 10 was fabricated by way of trial as Comparative Example 1. Experiments to investigate characteristics of the electrodes were conducted on Example 1 and Comparative Example 1.
(Fabrication of Pharmacologic Measurement Instrument)

First of all, description will be given of a fabrication method for the sensor base substrate 16 and the solution holding section 17 of the well vessel 19.

The sensor base substrates 16 of Example 1 and Comparative Example 1 were fabricated using a 4 inch SOI wafer as base substrate material. A front surface of the base substrate was dry etched to form a group of through holes with RIE. A back surface of thereof was etched by anisotropic wet etching using TMAH (tetramethyl ammonium) to thereby complete through holes between the front and back surfaces. All the base substrate was thermally oxidized to form $SiO_2$ layers on the front surface and the outermost surface of a device. Thereafter the wafer was diced into small square pieces each having a side of 30 mm in length and electrodes were patterned on the $SiO_2$ layer at the back surface of the base substrate in the shape of a small square piece using a vacuum evaporation method or a sputtering method. Gold was used as an electrode material. Thereby, 16 electrodes are patterned on the base substrate in the shape of a square having a side of 30 mm in length and 100 through holes were formed for each electrode to thereby form a sensor base substrate.

An ABS resin piece cut into a square piece having a side of 30 mm in length and a thickness of 5 mm was used as the upper base 102 of the solution holding section 17 of Example 1. On the ABS resin piece 102, a tapered hole having the upper surface diameter of 3 mm in length and the lower surface diameter of 1 mm in length is cut at a position corresponding to each of the electrodes (16 sites) to form recesses 4. Thereafter, masking was applied on the lower surface and side surface and chemical copper was electroless plated on the ABS resin piece 102 as an underlying layer and thereafter, gold was plated thereon. Thereafter, masking was peeled off and a tapered cutting tool slightly obtuser-angled than the taper of the tapered hole was used to thereby cut off a metal layer formed by plating in the vicinity of the lower surface on the hole sidewall of the ABS resin piece 102. Thereby, the reference electrode 13 was formed on the entire top surface of the upper surface and an upper portion of the wall surface of a solution recess of the solution holding section 17. The solution holding section 17 was adhered to the sensor base substrate 16 using a thermowelding sheet NS-100 (manufactured by NITTO SHINKO Corporation).

On the other hand, a platinum strand having a diameter of 0.5 mm was used as the reference electrode 131 of the sensor base substrate of Comparative Example 1. The reference electrode 13 was in similar way immersed in a recess of the sensor base substrate to which the solution holding section made of ABS resin is attached to thereby conduct measurement.

The electrically conductive box was made of aluminum. An opening in the shape of a square having a side of 25 mm in length was formed at the top surface thereof. In Example 1, the well vessel 19 is mounted so as to be accommodated in the opening section 8 and the electrically conductive box 2 and the reference electrode 13 of the well vessel 19 was electrically connected to each other. A preamplifier (the first signal amplifier) 3 was fabricated in the electrically conductive box 2 right under the well vessel 19 using AD 620 (manufactured by Analog Devices Inc.). Power supply to the preamplifier was done by 18 V dry battery.

Figure 10:
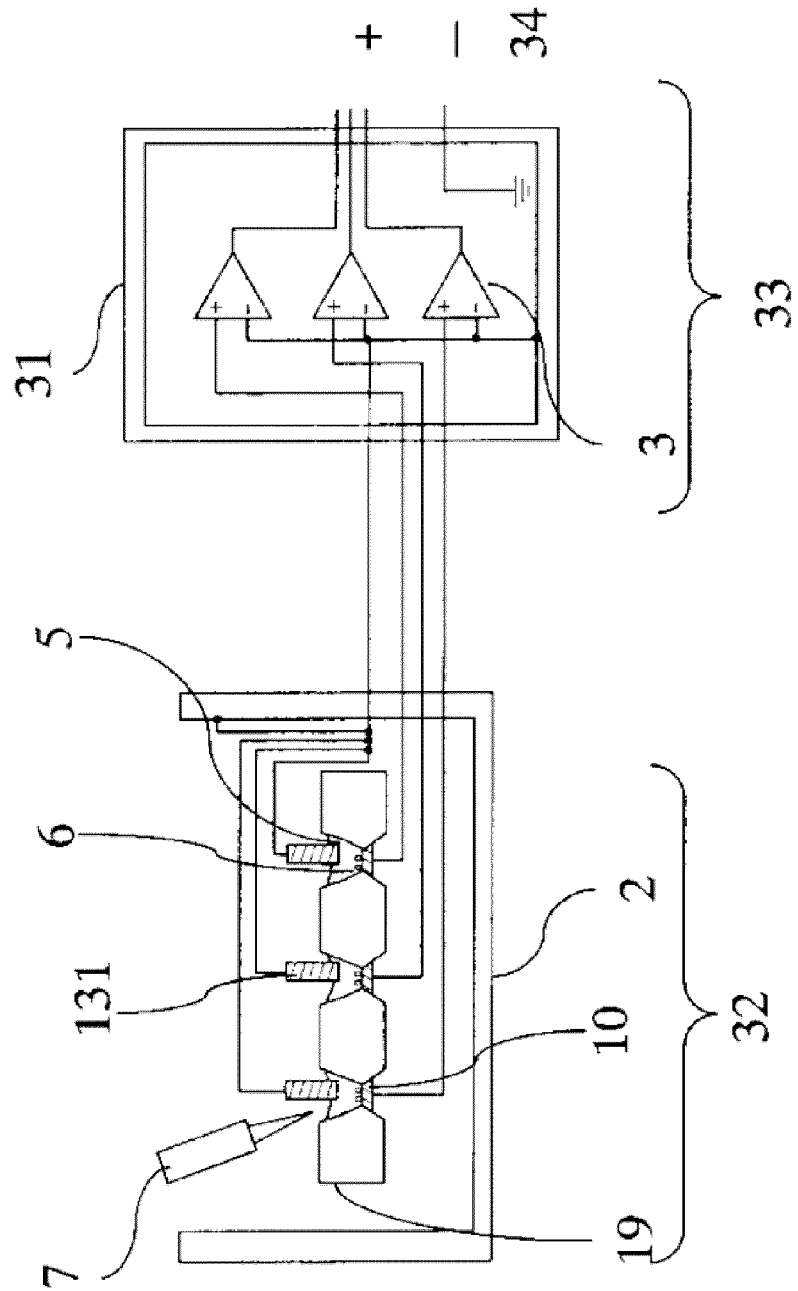
FIG. 10 is a conceptual view, as a mode, showing a construction of a pharmacologic measurement instrument of Comparative Example 1.

In a case of Comparative Example 1, the well vessel 19 is, as shown in FIG. 10, disposed in the electrically conductive box 2. The top part of the electrically conductive box 2 was opened for injection/discharge of a medicinal solution. In Comparative Example 1, the preamplifier 3 is disposed in a preamplifier shield 31 provided separately from the electrically conductive box 2. That is, the device section 32 and the preamplifier section 33 are installed separately from each other.

As a cell, there was used a human embryonic kidney cell HEK-293 (hereinafter referred to as HEK) revealing a carbachol (hereinafter referred to as CCh) sensitive ion channel by inheritable genetic modification technology. The solution holding section 17 was filled with a culture fluid and 8000 HEK cells are seeded in the holding section in dispersion. The culture fluid used was HEPES buffer DMEM+10 wt % FBS. A cell was sucked from the back surface to be thereby fitted into the hole and thereafter, the culture fluid was replaced with a measurement solution. A composition of the measurement solution was such that Ringer's solution was contained as a base, a Ca concentration was adjusted to 2 mM and an osmotic pressure was set to 300 Osm.

Figure 11:
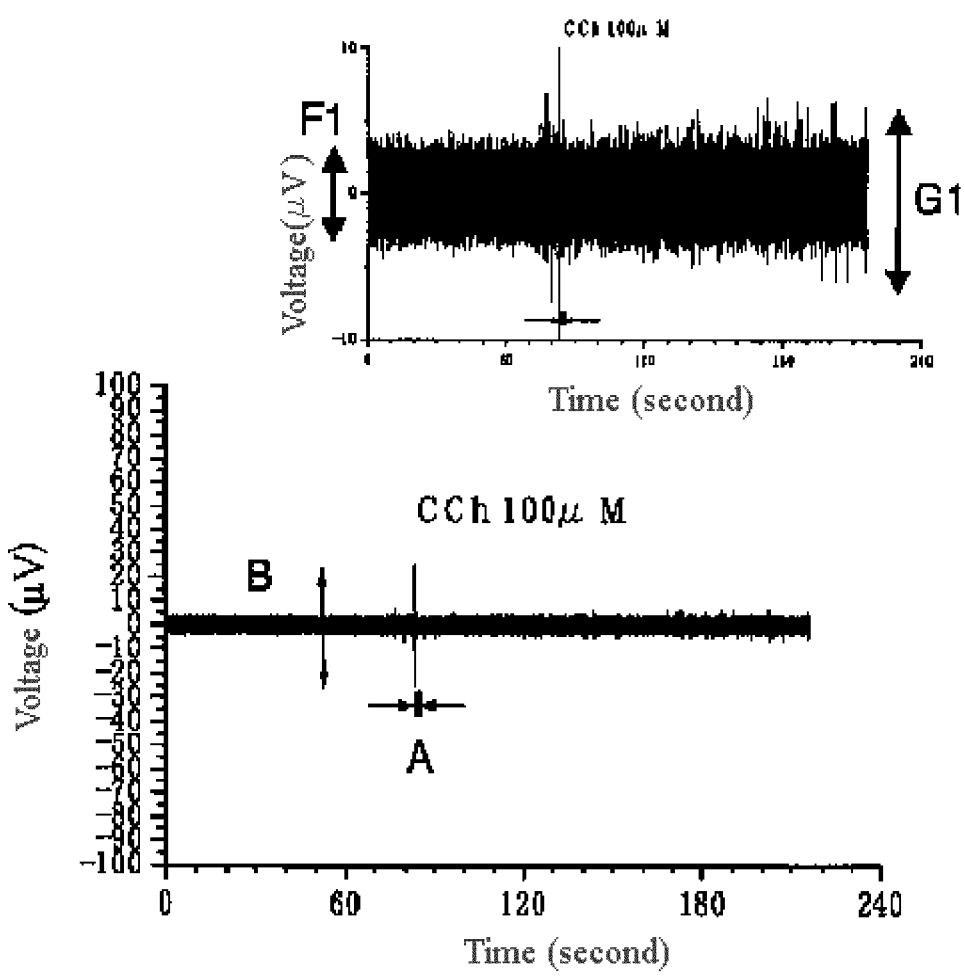
FIG. 11 is a graph showing results of voltage measurement in Example 1.

FIG. 11 is a graph showing a voltage noise when the above Ringer's solution was replaced with a Ringer's solution containing CCh 100 μM using Example 1. The inset graph in FIG. 11 shows an enlarged version of the original graph with respect to Y axis. It was recognized that a voltage noise is increased by CCh dropping (in FIG. 11, between F1 and G1). On the other hand, in FIG. 12, there is shown results obtained by conducting a similar experiment in a convention method (Comparative Example 1). The measurement was obtained in a procedure in which a first stage amplification in the preamplifier was multiplication by a factor of 100 and thereafter further amplified by a factor of 100. LPF was set at 5 kHz. A medicine (CCh) was dropped only for a time expressed with an open square in the figure.

TABLE 1

Figure 12:
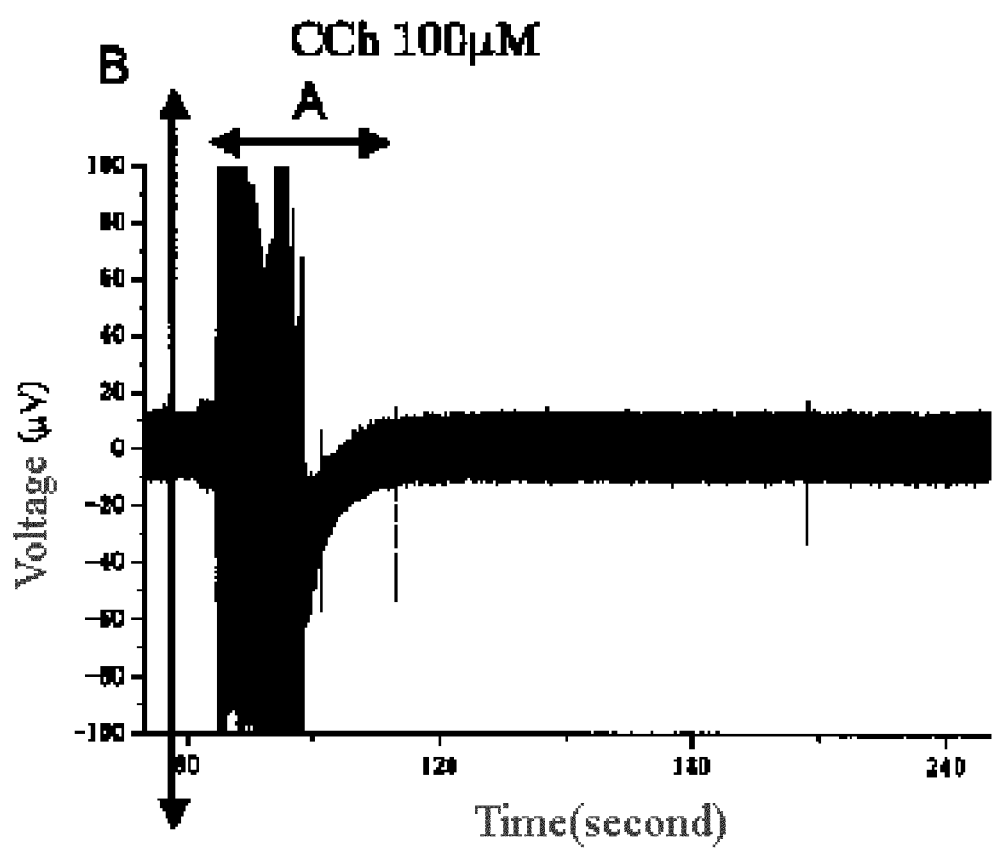
FIG. 12 is a graph showing results of voltage measurement in Comparative Example 1.

|  | Comparative Example 1 (FIG. 11) | Example 1 (FIG. 12) |
|---|---|---|
| Average value of noise amplitude when normal (μVrms) | 7.3 | 1.0 |
| Noise increase factor when a medicine was dropped (a factor of noise amplification over while normal) [B in FIGS. 11 and 12] | 109 | 1.41 |
| A recovery time while medicine | 30 | 0.4 |

TABLE 1-continued

|  | Comparative Example 1 (FIG. 11) | Example 1 (FIG. 12) |
|---|---|---|
| being dropped (sec) [A in FIGS. 11 and 12] |  | 5 |

Changes in external disturbance accompanying medicine dropping were compiled in Table 1. In Comparative Example 1, an amplitude of external noise (B in FIG. 12) due to replacement with a new solution is, as shown in Table 1, about 800 $\mu V_{p-p}$, which is about 109 times as large as the average value of noise amplitudes while in a normal mode. Recovery of a voltage value (A in FIG. 12) after exchange of solutions takes about 30 sec. On the other hand, in Example 1, a noise amplitude while in a normal mode decreases to 6 $\mu V_{p-p}$ (1 $\mu V$rms), an external disturbance noise amplitude value due to replacement with a new solution decreases to 8.4 $\mu V_{p-p}$ and a voltage value due to exchange of solutions is recovered in about 0.4 sec. Therefore, with a construction of the invention adopted, a noise amplitude while in a normal mode decreases to a value about 1/7 time as large as the amplitude in a normal mode, thereby enabling external disturbance while a medicine is dropped to be stabilized to a value smaller than otherwise by a factor of about 100. A recovery time of an electric signal after a medicine is dropped can be decreased to a value smaller than in a normal mode by a factor of 75 and with such an improvement, it is possible to capture a change in ion channel inactivated in several sec after a medicine is dropped.

Figure 13:
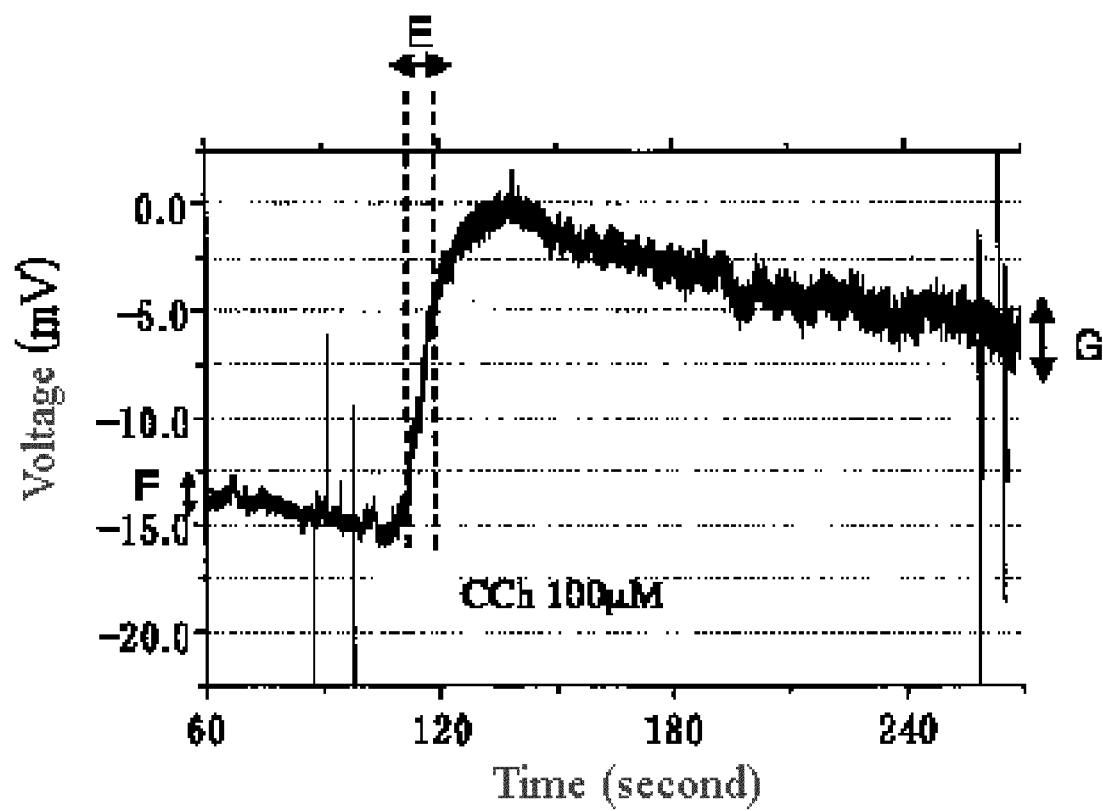
FIG. 13 is a graph showing results of measurement in Comparative Example 2.

In FIG. 13, as Comparative Example 2, there is shown results obtained by measurement of a response of an intracellular potential in an HEK cell for the same medicine in a similar way while a glass patch pipette is attached to the cell using a patch clamp method, which is a conventional method for measurement of an intracellular potential. A CCh concentration was 100 $\mu M$ in a similar way. An intracellular potential is, as shown in FIG. 13, depolarized by about 10 mV in 6 sec after CCh is dropped. There is observed a noise change (from F to G in FIG. 13) due to a CCh sensitive channel response.

The CCh reaction cannot be captured in Comparative Example 1. It was shown that in order to capture a medicine response of a cell represented by a CCh reaction with an electrode outside a cell, the construction of Example 1 is indispensably adopted.

The invention can be used in measurement of a change in electric signal caused by a phamacologic action or an electrophysiologic action of a biologic specimen.

what is claimed is:

1. A pharmacologic measurement instrument for measuring an electric signal caused by a pharmacologic action or electrophysiologic action of a biologic specimen, the pharmacologic measurement instrument comprising:
   an electrically conductive box provided with an opening section; and
   a well vessel disposed in the opening section,
   wherein the well vessel comprises:
   a base substrate provided with one or more well recesses in which one or more biologic specimens are placed;
   one or more measurement electrodes provided on bottom surfaces or back surfaces of the respective one or more well recesses; and
   a reference electrode electrically insulated from the respective one or more measurement electrodes,
   the reference electrode being formed on a top surface of the well vessel except for the bottom surfaces of the one or more well recesses and areas in the vicinities thereof,
   the well vessel being disposed inside the electrically conductive box in such a manner that the well vessel blocks the opening section entirely,
   the reference electrode being electrically connected with the electrically conductive box.

2. The pharmacologic measurement instrument according to claim 1, wherein said reference electrode is formed so as to cover the top surface of said well vessel entirely, and a circumference of said reference electrode on the top surface makes contact with a surrounding portion of said opening section.

3. The pharmacologic measurement instrument according to claim 1, further comprising one or more first signal amplification sections provided inside of said electrically conductive box, wherein one input terminal of each of said first signal amplification sections is connected to a corresponding one of said one or more measurement electrodes and the other input terminal of each of said first signal amplification sections is connected to the reference electrode.

4. The pharmacologic measurement instrument according to claim 1, further comprising a base substrate placement table for fixing said well vessel, said base substrate placement table having one or more contact points each contacting a corresponding one of said one or more measurement electrodes.

5. The pharmacologic measurement instrument according to claim 1, further comprising one or more injection/discharge devices each capable of injecting a solution containing the biologic specimen into a corresponding well recess and discharging the solution from the corresponding well recess, the one or more injection/discharge devices being arranged in a sliding manner to inject the solution into the one or more well recesses and discharge the solution from the one or more well recesses.

6. The pharmacologic measurement instrument according to claim 1, wherein an insulating section is provided between each of one or more the measurement electrodes and the reference electrode, and
   wherein the insulating sections have no toxicity to the biologic specimen.

7. The pharmacologic measurement instrument according to claim 1, wherein each of the one or more well recesses has an inversely tapered sidewall with a diameter of each of the one or more well recesses increasing upwardly,
   wherein the reference electrode extends into the recess sidewall of each of the one or more well recesses, and
   wherein an insulating section is provided between each of the one or more measurement electodes and the reference electrode by removing a part of the reference electrode in a vicinity of the corresponding recess sidewall and adjacent to the corresponding measurement electrode located at the bottom surface of the corresponding well recess.

8. The pharmacologic measurement instrument according to claim 1, wherein a through hole is provided in the bottom surface of each of the one or more well recesses, and
   wherein each of the is arranged in a respective through hole of the one or more well recesses so as to connect to a biologic specimen fixed in the corresponding through hole.

9. The pharmacologic measurement instrument according to claim 8, further comprising suction means for guiding the biologic specimen into a corresponding through hole of the one or more well recesses.

10. The pharmacologic measurement instrument according to claim 1, wherein a solution to be accommodated in the one or more well recesses can be exchanged for another solution.

11. The pharmacologic measurement instrument according to claim 1, wherein the well vessel is mountable or demountable through the opening section of the electrically conductive box and is disposable.

12. A pharmacologic measurement system which comprises:
   the pharmacologic measurement instrument according to claim 3; and
   a calculation section for data-processing a signal amplified in each of said first signal amplification sections.

13. The pharmacologic measurement system according to claim 12, further comprising a second signal amplification section for further amplifying an output signal from each of the one or more measurement electrodes, already amplified in the corresponding first amplification section, while causing band limitation thereto.

14. The pharmacologic measurement system according to claim 12, further comprising an electric stimulus generator for applying a desired current at a desired timing to each of the one or more measurement electrodes.

15. The pharmacologic measurement system according to claim 12, further comprising a measurement environment adjustment apparatus for adjusting a temperature, a humidity and a gas concentration of the pharmacologic measurement instrument to respective desired values.

16. A method for measuring an electric signal caused by a pharmacologic action or electrophysiologic action of a biologic specimen with a pharmacologic measurement instrument,
   wherein the pharmacologic measurement instrument includes
   (i) an electrically conductive box provided with an opening section, and
   (ii) a well vessel, the well vessel including
      (a) a base substrate provided with one or more well recesses,
      (b) one or more measurement electrodes provided on bottom surfaces or back surfaces of the respective one or more well recesses, and
      (c) a reference electrode electrically insulated from the respective one or more measurement electrodes, the reference electrode being formed on a top surface of the well vessel except for the bottom surfaces of the one or more well recesses and areas in the vicinities thereof, and
   wherein the method comprises:
      (i) supplying the biologic specimen into the respective one or more well recesses;
      (ii) disposing the well vessel inside the electrically conductive box so as to block the opening section entirely with the well vessel and connect the reference electrode electrically with the electrically conductive box; and
      (iii) after said supplying operation and said disposing operation, measuring the electric signal with the one or more measurement electrodes and the reference electrode.

17. The method according to claim 16, wherein said supplying operation is performed before said disposing operation is performed.

18. The method according to claim 16, wherein said disposing operation is performed before said supplying operation is performed.

19. A method for measuring an electric signal caused by a pharmacologic action or electrophysiologic action of a biologic specimen with a pharmacologic measurement instrument, the method comprising:
   providing a pharmacologic instrument including
      (i) an electrically conductive box provided with an opening section, and
      (ii) a well vessel, the well vessel including
         (a) a base substrate provided with one or more well recesses,
         (b) one or more measurement electrodes provided on bottom surfaces or back surfaces of the respective one or more well recesses, and
         (c) a reference electrode electrically insulated from the respective one or more measurement electrodes, the reference electrode being formed on a top surface of the well vessel except for the bottom surfaces of the one or more well recesses and areas in the vicinities thereof;
   supplying the biologic specimen into the respective one or more well recesses;
   disposing the well vessel inside the electrically conductive box so as to block the opening section entirely with the well vessel and conduct the reference electrode electrically with the electrically conductive box; and
   after said supplying operation and said disposing operation, measuring the electric signal with the one or more measurement electrodes and the reference electrode.

20. The method according to claim 19, wherein said supplying operation is performed before said disposing operation is performed.

21. The method according to claim 19, wherein said disposing operation is performed before said supplying operation is performed.

* * * * *